United States Patent [19]

Walker

[11] 4,293,561
[45] * Oct. 6, 1981

[54] 1-(NAPHTHYL-N-PROPYL)IMIDAZOLE DERIVATIVES

[75] Inventor: Keith A. M. Walker, Los Altos Hills, Calif.

[73] Assignee: Syntex (U.S.A.) Inc., Palo Alto, Calif.

[*] Notice: The portion of the term of this patent subsequent to Apr. 17, 1996, has been disclaimed.

[21] Appl. No.: 19,201

[22] Filed: Mar. 9, 1979

[51] Int. Cl.³ .................. A61K 31/415; C07D 233/60; C07D 405/06
[52] U.S. Cl. .............................. 424/273 R; 548/336; 548/341
[58] Field of Search .......................... 548/341, 336; 424/273 R

[56] References Cited

U.S. PATENT DOCUMENTS

| | | | |
|---|---|---|---|
| 4,085,209 | 4/1978 | Miller et al. | 548/341 |
| 4,141,908 | 2/1979 | Heeres | 548/336 |
| 4,150,153 | 4/1979 | Walker | 548/341 |
| 4,156,008 | 5/1979 | Heeres | 548/336 |
| 4,172,141 | 10/1979 | Walker | 548/341 |

Primary Examiner—Henry R. Jiles
Assistant Examiner—Natalia Harkaway
Attorney, Agent, or Firm—Annette M. Moore; Alan M. Krubiner

[57] ABSTRACT

Compounds of the formula

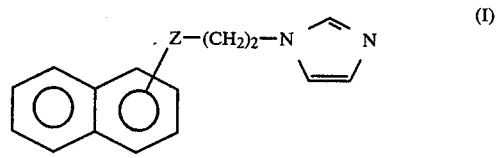

wherein Z is $C_1$ and $C_4$ alkoxymethylene, hydroxymethylene, esterified hydroxymethylene, carbonyl, or ketal-protected carbonyl, and the pharmaceutically acceptable acid addition salts thereof, are useful as anti-convulsant and anti-secretory agents.

7 Claims, No Drawings

1-(NAPHTHYL-N-PROPYL)IMIDAZOLE DERIVATIVES

DESCRIPTION OF THE INVENTION

The present invention relates to certain 1-(naphthyl-n-propyl)imidazole derivatives. More particularly, the present invention relates to compounds of formula (I), namely:

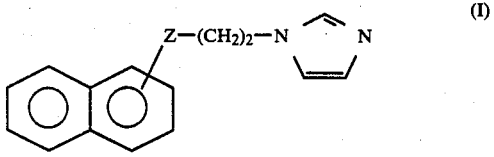

wherein Z is hydroxymethylene, esterified hydroxymethylene, $C_1$ to $C_4$ alkoxymethylene, carbonyl, of ketal-protected carbonyl; and the pharmaceutically acceptable acid addition salts thereof.

As used in the specification and appended claims, unless specified to the contrary, the following terms have the meanings indicated. The term "esterified hydroxymethylene" refers to a hydroxymethylene group which has been esterified with an alkanoic acid having from 1 to 8 carbon atoms or with benzoic acid. Typical alkanoic acids which may be mentioned are formic acid, acetic acid, propionic acid, butyric acid, isobutyric acid, valeric acid, isovaleric acid, caproic acid and octanoic acid. The term "alkoxymethylene" refers to a hydroxymethylene group which has been alkylated on oxygen with a straight or branched chain group having from 1 to 4 carbon atoms. Representative of such alkyl groups are methyl, ethyl, isopropyl, n-butyl, etc. The term "ketal-protected carbonyl" refers to (i) a carbonyl group protected as an acyclic ketal derived from a monohydric straight chain alkanol having from 1 to 4 carbon atoms such as, for example, the dimethyl-, diethyl-, di(n-propyl)-and di(n-butyl)ketals, and (ii) a carbonyl group protected as a cyclic ketal derived from a dihydric alcohol having 2 or 3 carbon atoms which may optionally be substituted by one or more methyl groups, for example, the ethylenedioxy-, 1,3-propylenedioxy-, 1,2-propylenedioxy-, 2,2-dimethyl-1,3-propylenedioxy-, 1-methyl-1,3-propylenedioxy-, 1,3-dimethyl-1,3-propylenedioxy- and 2,3-butylenedioxyketals. The term "pharmaceutically acceptable acid addition salts" refers to salts of the free bases of formula (I), which salts possess the desired pharmacological activity and which are neither biologically nor otherwise undesirable. Such salts may be formed with inorganic acids such as hydrochloric acid, hydrobromic acid, sulfuric acid, nitric acid or phosphoric acid; or with organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

Compounds of formula (I) wherein Z is hydroxymethylene, esterified hydroxymethylene or alkoxymethylene possess a chiral center. Accordingly, these compounds may be prepared in either optically active form, or as a racemic mixture. Unless otherwise specified, the compounds described herein are all in the racemic form. However, the scope of the subject invention is not to be limited to the racemic form but is to encompass the individual optical isomers of the subject compounds.

If desired, compounds of formula (I) wherein Z is hydroxymethylene, esterified hydroxymethylene or alkoxymethylene may be prepared in optically active form by conventional resolution means known per se, for example, by the separation (e.g., fractional crystallization) of the diastereomeric salts formed by reaction of, e.g., racemic compounds of formula (I) wherein Z is hydroxymethylene or esterified hydroxymethylene, or alkoxymethylene with an optically active acid, or by separation of the diastereomeric esters formed by reaction of such a racemic alcohol wherein Z is hydroxymethylene with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the desired compound.

Compounds of formula (I) exhibit a broad spectrum of CNS related activity such as anticonvulsant activity (as demonstrated by the maximal electroshock seizure test), anorexigenic, antidepressant and muscle relaxing activity; as well as activity of other types such as inhibition of gastric secretion, antihypertensive and spermatostatic/spermatocidal activities.

One aspect of the present invention relates to a method for treating and/or preventing convulsions in a mammalian subject comprising administering a therapeutically effective amount of a compound of formula (I), or a pharmaceutically acceptable acid addition salt thereof. Another aspect of the present invention relates to pharmaceutical compositions useful for the treatment and/or prevention of convulsions in a mammalian subject comprising a compound of formula (I), or a pharmaceutically acceptable acid addition salt thereof, in admixture with a pharmaceutically acceptable non-toxic carrier. For this utility compounds of formula (I) wherein Z is carbonyl, ketal-protected carbonyl or alkoxymethylene are particularly preferred.

Yet another aspect of the present invention relates to a method for inhibiting gastric secretion in a mammalian subject comprising administering a therapeutically effective amount of a compound of formula (I), or a pharmaceutically acceptable acid addition salt thereof. Still another aspect of the present invention relates to pharmaceutical compositions useful for the inhibition of gastric secretion in a mammalian subject comprising a compound of formula (I), or a pharmaceutically acceptable acid addition salt thereof, in admixture with a pharmaceutically acceptable non-toxic carrier.

In the practice of the above described methods of the present invention a therapeutically effective amount of the compound of formula (I) or a pharmaceutical composition containing same is administered via any of the usual and acceptable methods known in the art, either singly or in combination with another compound or compounds of the present invention or other pharmaceutical agents. These compounds or compositions can thus be administered orally or parenterally (i.e. intramuscularly, subcutaneously and intravenously), and can be administered either in the form of solid or liquid dosages including tablets, solutions, suspensions, and the like, as discussed in more detail hereinbefore. Oral administration is preferred. The administration can be conducted in a single unit dosage form the continuous therapy or in single dosage therapy ad libitum. The method of the present invention may be practiced when relief of symptoms is specifically required, i.e. therapeutically, or as continuous or prophylactic treatment.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount for anticonvulsant use ranges from about 0.1 to about 300 mg./kg. body weight per day. In alternate terms, for an average adult human subject, a therapeutically effective amount in accordance herewith would be, in preferred embodiments, from about 70 mg. to about 7 g per day per subject. A therapeutically effective amount for inhibition of gastric secretion ranges from about 0.1 to about 300 mg./kg. body weight per day and preferably from about 0.25 to about 100 mg./kg. body weight per day. In alternate terms, for an average adult human subject, a therapeutically effective amount in accordance herewith would be, in preferred embodiments from about 18 mg. to about 7 g per day per subject.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject.

Compounds related to those of formula (I) have been previously described in applicant's co-pending application Ser. No. 848,548, filed Nov. 4, 1977 now U.S. Pat. No. 4,150,153, issued Apr. 17, 1979, as intermediates for the preparation of compounds having anti-fungal, anti-bacterial and antiprotozoal activity. The disclosure in said co-pending application is hereby incorporated by reference herein.

The compounds of the present invention may be prepared according to methods well known in the art. For example, compounds of formula (I) wherein Z is carbonyl may be prepared in a manner analogous to that described in U.S. Pat. No. 4,078,071 to the applicant for the corresponding phenyl compounds. This method comprises reacting a haloethyl naphthyl ketone, or a vinyl naphthyl ketone or the Mannich base quaternary intermediate thereof with imidazole in an inert organic solvent. The starting haloethyl naphthyl ketones are known or may be prepared by the Friedel-Crafts reaction of naphthalene with β-chloropropionyl chloride. Vinyl ketones, insofar as they may not be known or generally available, may be prepared by a variety of methods well known in the synthetic organic chemistry art, for example, by the addition of vinyl lithium to the corresponding carboxylic acid; by the addition of vinyl lithium to the corresponding aldehyde followed by oxidation of the allylic alcohol thus produced to the vinyl ketone (e.g., *J. Chem. Soc (C)*, 1966, p. 1972; *J. Chem Soc. (London)*, 1956, p. 3070); or by Mannich reaction of the corresponding methyl ketone, quaternization and elimination. The preparation of ketones of formula (I) by the above described method may be carried out in an inert organic solvent, for example, dimethylformamide at a temperature between about −10° and +40° C.

Preparation of compounds of formula (I) wherein Z is hydroxymethylene may be accomplished by the reduction of the corresponding ketone or acid addition salt thereof under standard conditions, for example, by the use of sodium tetrahydroborate in a protic solvent, for example, methanol, at a temperature between about −20° and +20° C.

Compounds of formula (I) wherein Z is esterified hydroxymethylene may be prepared under usual esterification conditions from the corresponding alcohol by treatment of the alcohol with the desired acid halide or anhydride in the presence of a base, preferably a tertiary amine such as pyridine or triethylamine, at a temperature between about 0° and +40° C. in a solvent such as pyridine, tetrahydrofuran, dichloromethane, chloroform, and the like.

Compounds of formula (I) wherein Z is ketal-protected carbonyl may be prepared according to the following reaction sequence:

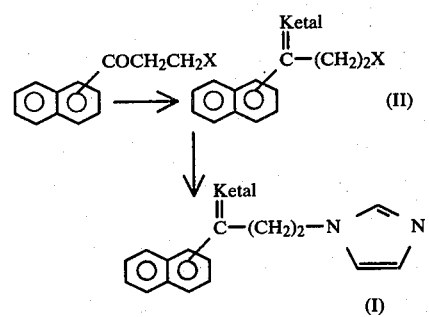

wherein X is halo (especially chloro or bromo).

In this sequence the naphthyl haloethyl ketone is first converted to the halo ketal (II). Ketalization to form cyclic ketals may be performed by methods well known in the art, e.g. by treatment of the ketone with the desired dihydric alcohol in the presence of a strong acid, for example a sulfonic acid such as p-toluene-sulfonic acid or a Lewis acid such as boron trifluoride. Water is preferably removed as an azeotrope with the solvent, for example an aromatic hydrocarbon such as benzene or toluene, at a temperature sufficient to effect such azeotropic removal, e.g. from about 75° to about 150° C. Ketalization to form acyclic ketals may be performed by employing an orthoester (e.g. methyl orthoformate or ethyl orthoformate) in the presence of an acid or Lewis acid, e.g. boron trifluoride, p-toluenesulfonic acid, perchloric acid, fuming sulfuric acid, and the like. The haloketal (II) is then converted to (I) by treatment with imidazole in a polar aprotic solvent such as dimethylformamide, dimethylsulfoxide acetonitrile or tetrahydrofuran at a temperature between about 20° and 130° C.

Compounds of formula (I) wherein Z is alkoxymethylene may be prepared by alkylation of the corresponding alcohols. The alkylation is carried out by converting the alcohol to a metal salt, preferably an alkali metal salt, by treatment with a strong base such as, for example, an (alkali) metal hydride such as sodium hydride or an (alkali) metal amide such as sodium amide or potassium amide and the like. This is preferably done in an inert organic solvent such as dimethylformamide, hexamethylphosphoramide, tetrahydrofuran and the like. The (alkali) metal salt is then contacted with an alkylating agent, e.g. an alkyl halide, sulfate or sulfonate ester, preferably an alkyl halide, preferably in the same solvent system, at a temperature between −20° and 100° C., most preferably between 0° and 60° C., for a period of 30 minutes to 18 hours.

The subject compounds of formula (I) can be isolated as free bases; however, since many of the compounds in base form are oils and gums and/or not water soluble it is often more convenient to isolate and further characterize such compounds as acid addition salts. These salts are prepared in the usual manner, i.e., by reaction of the free base with a suitable inorganic or organic acid, for example one of the pharmaceutically acceptable acids described above. If desired, the salt can be readily converted to the free base by treatment with a base such as potassium or sodium carbonate or potassium or sodium hydroxide.

Especially preferred are the following compounds:
1-[2-(2-naphthoyl)ethyl]imidazole;
1-[3-hydroxy-3-(2-naphthyl)-n-propyl]imidazole;
1-[3-methoxy-3-(2-naphthyl)-n-propyl]imidazole;
1-[3-acetoxy-3-(2-naphthyl)-n-propyl]imidazole;
1-[3-benzoyloxy-3-(2-naphthyl)-n-propyl]imidazole;
1-[3,3-ethylenedioxy-3-(2-naphthyl)-n-propyl]imidale; and
1-[2-(1-naphthoyl)ethyl]imidazole.

A further aspect of the present invention concerns a process for the preparation of a free base compound of the formula

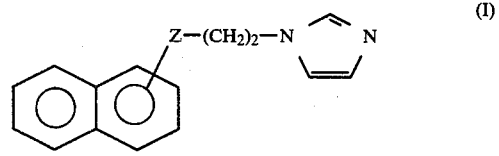

wherein Z is hydroxymethylene, esterified hydroxymethylene, ($C_1$ to $C_4$) alkoxymethylene, carbonyl, or ketal-protected carbonyl; or a pharmaceutically acceptable non-toxic acid addition salt thereof, which process comprises:

(a) the preparation of a compound of formula (I) wherein Z is carbonyl by reaction of a β-haloethyl naphthyl ketone or a naphthyl vinyl ketone, or the Mannich base quaternary intermediate with imidazole, or (b) the preparation of a compound of formula (I) wherein Z is hydroxyethylene by reduction of a compound of formula (I) wherein Z is carbonyl, or (c) the preparation of a compound of formula (I) wherein Z is esterified hydroxymethylene by esterification of a compound of formula (I) wherein Z is hydroxymethylene, or (d) the preparation of a compound of formula (I) wherein Z is $C_1$ to $C_4$ alkoxymethylene by alkylation of a compound of formula (I) wherein Z is hydroxymethylene, or (e) the preparation of a compound of formula (I) wherein Z is ketal-protected carbonyl by reaction of a compound of the formula

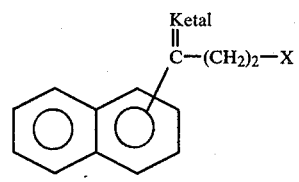

wherein X is halo, with imidazole or an alkali metal salt thereof, or (f) optionally converting a free base to the corresponding acid addition salt, or (g) optionally converting an acid addition salt to the corresponding free base.

The following specific description is given to enable those skilled in the art to more clearly understand and practice the present invention. It should not be considered as a limitation upon the scope of the invention but merely as illustrative and representative thereof.

PREPARATION 1

A solution of 34 g of 2-acetonaphthone, 13.5 g of paraformaldehyde, 24.46 g of dimethylamine hydrochloride and 0.2 ml of concentrated hydrochloric acid in 100 ml ethanol is heated under reflux for 24 hours. The solvent is removed and the resulting white solid, 2-naphthyl 2-dimethylaminoethyl ketone hydrochloride is recrystallized twice from acetone/methanol. The hydrochloride salt (31.3 g) is neutralized with aqueous potassium carbonate solution, extracted with ether, dried ($MgSO_4$) and filtered. Treatment of the ethereal solution with 15 ml of iodomethane causes precipitation of [2-(2-naphthoyl)ethyl]trimethylammonium iodide, as a white solid, washed with acetone and dried in air.

Yield: 35.5 g.

EXAMPLE 1

To a stirred, ice-cooled solution of 4.76 g of imidazole in 30 ml of dry dimethylformamide is added 17.66 g of crude [2-(2-naphthoyl)ethyl]trimethylammonium iodide. The mixture is stirred overnight at room temperature and at 75° C. for one day. The resulting solution is poured into water and the precipitate filtered off, washed with water and dried in air. The resulting 1-[2-(2-naphthoyl)ethyl]imidazole is dissolved in ethyl acetate and converted to its hydrochloride acid addition salt by addition of ethereal hydrogen chloride until precipitation is complete. The crude salt (11.3 g) is recrystallized from methanol/acetone to yield colorless crystals of 1-[2-(2-naphthoyl)ethyl]imidazole hydrochloride, m.p. 182.5°–186° C.

Similarly prepared using the corresponding [2-(1-naphthoyl)ethyl]trimethylammonium iodide is 1-[2-(1-naphthoyl)ethyl]imidazole and its hydrochloride salt.

EXAMPLE 2

To 2.86 g of the above obtained 1-[2-(2-naphthoylethyl]imidazole hydrochloride in 150 ml of methanol at 0°–5° C. is added, with stirring, excess sodium tetrahydroborate. After stirring overnight at room temperature, the reaction mixture is evaporated to dryness. The resulting residue is treated with 20 ml of water, the product extracted with ether and the extracts washed, dried (MgSO$_4$) and evaporated. The resulting colorless oil crystallizes on addition of ether and scratching, and is recrystallized from ethyl acetate to give 2.4 g of 1-[3-hydroxy-3-(2-naphthyl)-n-propyl]imidazole. The hydrochloride salt is prepared by treatment of an ethereal solution of the free base with ethereal hydrogen chloride until precipitation is complete. The precipitate is collected and recrystallized from methanol/acetone to give 1-[3-hydroxy-3-(2-naphthyl)-n-propyl]imidazole hydrochloride, m.p. 166.7°–168.1° C.

Similarly prepared from 1-[2-(1-naphthoyl)ethyl]imidazole hydrochloride is 1-[3-hydroxy-3-(1-naphthyl)-n-propyl]imidazole and its hydrochloride salt.

EXAMPLE 3

A solution of 1.2 g of 1-[3-hydroxy-3-(2-naphthyl)-n-propyl]imidazole in 20 ml of dry hexamethylphosphoramide is treated between 5°–10° C. with stirring under nitrogen with 0.24 g of a 50% dispersion of sodium hydride in mineral oil. The mixture is stirred one hour at 10° C., one hour at 50° C., and then cooled in ice. Methyl iodide (0.8 g.) in 2 ml of hexamethylphosphoramide is added with stirring maintaining the temperature below 10° C. and the mixture stirred at 5° C. for 1 hour and overnight at room temperature. The resulting mixture is poured into water, the product extracted with ether and the extracts washed, dried (MgSO$_4$) and evaporated to give a yellow oil. Chromatography on silica gel eluting with 10% methanol in dichloromethane gives pure 1-[3-methoxy-3-(2-naphthyl)-n-propyl]imidazole. This is converted to its hydrogen sulfate addition salt by dropwise addition of sulfuric acid to a solution in ether and recrystallized from methanol/ethyl acetate to give 1-[3-methoxy-3-(2-naphthyl)-n-propyl]imidazole hydrogen sulfate, m.p. 122°–122.5° C.

EXAMPLE 4

A solution of 1.36 g of 2-chloroethyl-2-naphthyl ketone, 6.05 g ethylene glycol and a crystal of p-toluenesulfonic acid monohydrate in 50 ml of toluene is heated for 8 hours under reflux through a Dean-Stark trap. After cooling, the mixture is neutralized by pouring into excess aqueous potassium carbonate, extracted with 200 ml ether and the organic phase washed, dried (MgSO$_4$), and evaporated to yield 2-(2-naphthyl)-2-(2-chloroethyl)-1,3-dioxolane. Without further purification the crude ketal (1.36 g.) is heated with 1.77 g of imidazole in 2 ml of acetonitrile at 85° overnight. The resulting mixture is evaporated to dryness, treated with water and the product extracted with ether. The extracts are washed well with water, dried (MgSO$_4$), evaporated and the residue chromatographed on silica gel eluting with 5% methanol/dichloromethane to give 0.78 g of 1-[3,3-ethylenedioxy-3-(2-naphthyl)-n-propyl]imidazole.

EXAMPLE 5

A solution of 1.26 g 1-[3-hydroxy-3-(2-naphthyl)-n-propyl]imidazole in 20 ml pyridine is treated dropwise with stirring with 0.72 ml of benzoyl chloride and the mixture stirred overnight. The resulting solution is poured into 100 ml water, extracted with ethyl acetate and the extracts washed, dried (MgSO$_4$) and evaporated in vacuo to remove residual pyridine and afford 1-[3-benzoyloxy-3-(2-naphthyl)-n-propyl]imidazole. The residue is dissolved in ether, treated with ethereal hydrogen chloride and the resulting precipitate recrystallized from acetone/methanol to give the hydrochloride salt.

EXAMPLE 6

Repeating the procedure of Example 4, utilizing the appropriate ketone and alkylene diol there may be prepared the following compounds which may be further characterized as the acid addition salts indicated:

1-[3,3-(1,3-propylenedioxy)-3-(2-naphthyl)-n-propyl]imidazole;
1-[3,3-(2,2-dimethyl-1,3-propylenedioxy)-3-(2-naphthyl)-n-propyl]imidazole;
1-[3,3-(1-methyl-1,3-propylenedioxy)-3-(2-naphthyl)-n-propyl]imidazole;
1-[3,3-ethylenedioxy-3-(1-naphthyl)-n-propyl]imidazole;
1-[3,3-(1,3-propylenedioxy)-3-(1-naphthyl)-n-propyl]imidazole;
1-[3,3-(2,2-dimethyl-1,3-propylenedioxy)-3-(1-naphthyl)-n-propyl]imidazole;
1-[3,3-(1-methyl-1,3-propylenedioxy)-3-(1-naphthyl)-n-propyl]imidazole;
1-[3,3-(1,2-propylenedioxy)-3-(2-naphthyl)-n-propyl]imidazole;
1-[3,3-(1,2-propylenedioxy)-3-(1-naphthyl)-n-propyl]imidazole;
1-[3,3-(2,3-butylenedioxy)-3-(2-naphthyl)-n-propyl]imidazole; and
1-[3,3-(2,3-butylenedioxy)-3-(1-naphthyl)-n-propyl]imidazole.

EXAMPLE 7

Repeating the procedure of Example 5, utilizing 1-[3-hydroxy-3-(2-naphthyl)-n-propyl]imidazole or 1-[3-hydroxy-3-(1-naphthyl)-n-propyl]imidazole, and the appropriate acid halide or anhydride, there may be prepared the following compounds:

1-[3-acetoxy-3-(2-naphthyl)-n-propyl]imidazole;
1-[3-propionyloxy-3-(2-naphthyl)-n-propyl]imidazole;
1-[3-butyryloxy-3-(2-naphthyl)-n-propyl]imidazole;
1-[3-isobutyryloxy-3-(2-naphthyl)-n-propyl]imidazole;
1-[3-hexanoyloxy-3-(2-naphthyl)-n-propyl]imidazole;
1-[3-acetoxy-3-(1-naphthyl)-n-propyl]imidazole;
1-[3-propionyloxy-3-(1-naphthyl)-n-propyl]imidazole;
1-[3-butyryloxy-3-(1-naphthyl)-n-propyl]imidazole;
1-[3-isobutyryloxy-3-(1-naphthyl)-n-propyl]imidazole;
1-[3-hexanoyloxy-3-(1-naphthyl)-n-propyl]imidazole; and;
1-[3-benzoyloxy-3-(1-naphthyl)-n-propyl]imidazole.

EXAMPLE 8

A solution of 2.18 g of 2-chloroethyl-2-naphthyl ketone, 1.7 g trimethyl orthoformate and a few crystals of p-toluenesulfonic acid (anhydrous) in 20 ml anhydrous methanol is heated under reflux for two hours. After cooling to room temperature, two drops of phenolphthalein solution are added and a solution of sodium methoxide in methanol is added dropwise until a pink color persists. After removal of the solvent under reduced pressure the resulting oil is dissolved in ether, decolorized with charcoal and the ether removal to give 2-chloroethyl-2-naphthyl ketone dimethyl ketal as a colorless oil.

2-Chloroethyl-2-naphthyl ketone dimethyl ketal 1.93 g in 5 ml acetonitrile is heated with 3.5 g of imidazole for 24 hours at 85° under nitrogen. The resulting solution is poured into water, extracted with ether and the extracts washed, dried (MgSO₄) and evaporated. After chromatography on silica gel eluting with 5% methanol/dichloromethane the product is recrystallized from toluene to give 1-[3-(2-naphthyl)-3,3-dimethoxy-n-propyl]imidazole as a colorless solid.

EXAMPLE 9

Repeating the procedure of Example 8, utilizing 2-chloroethyl 2-naphthyl ketone or 2-chloroethyl 1-naphthyl ketone and the appropriate alkyl orthoformate, there may be prepared the following compounds:
1-[3-(2-naphthyl)-3,3-diethoxy-n-propyl]imidazole;
1-[3-(2-naphthyl)-3,3-di(n-propoxy)-n-propyl-]imidazole;
1-[3-(2-naphthyl)-3,3-di-(n-butoxy)-n-propyl]imidazole;
1-[3-(1-naphthyl)-3,3-dimethoxy-n-propyl]imidazole;
1-[3-(1-naphthyl)-3,3-diethoxy-n-propyl]imidazole;
1-[3-(1-naphthyl)-3,3-di(n-propoxy)-n-propyl-]imidazole; and
1-[3-(1-naphthyl)-3,3-di(n-butoxy)-n-propyl]imidazole.

EXAMPLE 10

Ethereal hydrogen chloride is added dropwise to a solution of 1.0 g 1-[2-(2-naphthoyl)ethyl]imidazole in 100 ml anhydrous benzene until precipitation is complete. The product is filtered, washed with ether, air dried and recrystallized from methanol/acetone to yield 1-[2-(2-naphthoyl)ethyl]imidazole hydrochloride, m.p. 182.5°–186° C.

In a similar manner, all compounds of formula (I) in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 11

1-[2-(2-Naphthoyl)ethyl]imidazole hydrochloride (1.0 g.) suspended in 50 ml of ether is stirred with excess dilute aqueous potassium carbonate solution until the salt is completely dissolved. The organic layer is then separated, washed twice with water, dried over magnesium sulfate and evaporated to yield 1-[2-(2-naphthoyl)ethyl]imidazole.

In a similar manner the acid addition salts of all compounds of formula (I) may be converted to the corresponding compounds in free base form.

EXAMPLE 12

The following illustrates a pharmaceutical composition for oral administration which may be prepared for the compounds of the present invention, e.g.
1-[2-(2-naphthoyl)ethyl]imidazole hydrochloride or
1-[3,3-ethylenedioxy-3-(2-naphthyl)-n-propyl-]imidazole,

| | parts by weight |
|---|---|
| Active compound | 200 |
| Magnesium stearate | 3 |
| Starch | 30 |
| Lactose | 116 |
| Polyvinylpyrrolidone | 3 |

The above ingredients are combined and granulated using methanol as the solvent. The formulation is then dried and formed into tablets (containing 200 mg of active compound each) with an appropriate tabletting machine.

What is claimed is:

1. A compound of the formula

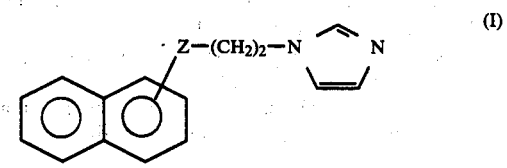

wherein Z is a carbonyl group protected as an acyclic ketal derived from a monohydric straight chain alkanol having from one to four carbon atoms, or a carbonyl group protected as a cyclic ketal wherein the cyclic ketal is selected from the group consisting of ethylenedioxy, 1,3-propylenedioxy, 1,2-propylenedioxy, 2,2-dimethyl-1,3-propylenedioxy, 1-methyl-1,3-propylenedioxy, 1,3-dimethyl-1,3-propylenedioxy, and 2,3-butylenedioxy and the pharmaceutically acceptable acid addition salts thereof.

2. The compound of claim 1 which is 1-[3,3-ethylenedioxy-3-(2-naphthyl)-n-propyl]imidazole and the pharmaceutically acceptable acid addition salts thereof.

3. The compound of claim 1 which is 1-[3,3-(1,3-propylenedioxy)-3-(2-naphthyl)-n-propyl]imidazole and the pharmaceutically acceptable acid addition salts thereof.

4. The compound of claim 1 which is 1-[3,3-ethylenedioxy-3-(1-naphthyl)-n-propyl]imidazole and the pharmaceutically acceptable acid addition salts thereof.

5. A pharmaceutical composition for the prevention and treatment of convulsions or inhibiting gastric secretion in mammals comprising a therapeutically effective amount of a compound of the formula

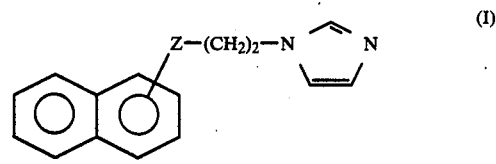

wherein Z is a carbonyl group protected as an acyclic ketal derived from a monohydric straight chain alkanol having from one to four carbon atoms, or a carbonyl group protected as a cyclic ketal wherein the cyclic ketal is selected from the group consisting of ethylenedioxy, 1,3-propylenedioxy, 1,2-propylenedioxy, 2,2-dimethyl-1,3-propylenedioxy, 1-methyl-1,3-propylenedioxy, 1,3-dimethyl-1,3-propylenedioxy, and 2,3-butylenedioxy or a pharmaceutically acceptable acid addition salt thereof; in admixture with a pharmaceutically acceptable, non-toxic carrier.

6. A method for treating and preventing convulsions in a mammalian subject comprising administering to said subject in need thereof a therapeutically effective amount of a compound of the formula

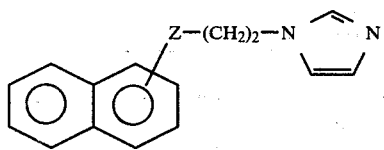

wherein Z is carbonyl, a carbonyl group protected as an acyclic ketal derived from a monhydric straight chain alkanol having from one to four carbon atoms, or a carbonyl group protected as a cyclic ketal derived from a dihydric alcohol having two or three carbon atoms which may be optionally substituted by one or more methyl groups or a pharmaceutically acceptable acid addition salt thereof.

7. A method for inhibiting gastric secretion in a mammalian subject comprising administering to said subject in need thereof a therapeutically effective amount of a compound of the formula

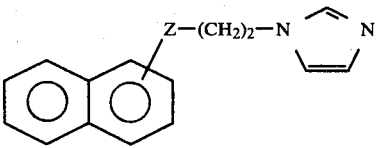

wherein Z is carbonyl, a carbonyl group protected as an acyclic ketal derived from a monhydric straight chain alkanol having from one to four carbon atoms, or a carbonyl group protected as a cyclic ketal derived from a dihydric alcohol having two or three carbon atoms which may be optionally substituted by one or more methyl groups or a pharmaceutically acceptable acid addition said thereof.

* * * * *